(12) United States Patent
Dietzel et al.

(10) Patent No.: US 9,265,510 B2
(45) Date of Patent: Feb. 23, 2016

(54) CONE LOCK QUICK CONNECT MECHANISM

(71) Applicant: Zimmer, Inc., Warsaw, IN (US)

(72) Inventors: Steven E. Dietzel, Peru, IN (US); Tim Yoko, Granger, IN (US); Anthony Romano, Columbia City, IN (US); Jeffery A. VanDiepenbos, Syracuse, IN (US); Nolan C. Jones, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 258 days.

(21) Appl. No.: 13/760,274

(22) Filed: Feb. 6, 2013

(65) Prior Publication Data

US 2013/0204260 A1  Aug. 8, 2013

Related U.S. Application Data

(60) Provisional application No. 61/595,384, filed on Feb. 6, 2012.

(51) Int. Cl.
*A61B 17/58* (2006.01)
*A61B 17/60* (2006.01)
*A61F 2/00* (2006.01)
*A61B 17/17* (2006.01)
*A61B 17/15* (2006.01)

(52) U.S. Cl.
CPC ............ *A61B 17/1764* (2013.01); *A61B 17/157* (2013.01)

(58) Field of Classification Search
CPC .......................... A61B 17/157; A61B 17/1764
USPC ............... 606/87–89, 96, 304, 323, 324, 328; 403/322.4, 374.5
See application file for complete search history.

(56) References Cited

U.S. PATENT DOCUMENTS

| | | | | |
|---|---|---|---|---|
| 4,487,532 | A  * | 12/1984 | Hamilton ......................... | 407/37 |
| 5,628,750 | A  * | 5/1997 | Whitlock et al. ................ | 606/88 |
| 6,699,293 | B2 * | 3/2004 | White .................. | A61F 2/30734 623/22.42 |
| 2003/0236525 | A1* | 12/2003 | Vendrely ................ | A61B 17/17 606/87 |
| 2006/0200162 | A1* | 9/2006 | Farling et al. ................... | 606/88 |

* cited by examiner

*Primary Examiner* — David Bates
*Assistant Examiner* — Olivia C Chang
(74) *Attorney, Agent, or Firm* — Schwegman Lundberg & Woessner, P.A.

(57) ABSTRACT

An apparatus includes a cut guide including a locking area, an alignment guide, and a connect mechanism to connect the cut guide to the alignment guide, wherein the connect mechanism includes a cone lock connect mechanism configured to engage with the cut guide locking area.

12 Claims, 13 Drawing Sheets

CONE LOCK QUICK CONNECT MECHANISM

CLAIM OF PRIORITY

This application claims the benefit of priority under 35 U.S.C. §119(e) of Yoko et al., U.S. Provisional Patent Application Ser. No. 61/595,384, entitled "CONE LOCK QUICK CONNECT MECHANISM", filed on Feb. 6, 2012, which is herein incorporated by reference in its entirety.

FIELD

The present patent application relates to an arthroplastic system and specifically to a connect mechanism for a tibial or femoral cut guide.

BACKGROUND

Orthopedic procedures for the replacement of all, or a portion of, a patient's joint typically require resecting (cutting) and reshaping of the ends of the bones of the joint. For instance, total knee replacement procedures typically involve resecting the distal end of the femur and the proximal end of the tibia prior to implanting the prosthesis components. Resecting the distal end of the femur often involves making several cuts of the distal end of the femur including a distal cut. Resecting the proximal end of the tibia often involves making a proximal cut.

Cut guides can be used to guide the saw and achieve the proper angle and position of these cuts. Cut guides can be in the form of blocks having slots therein for receiving and guiding the saw. In use, the block can be positioned against the bone with the help of positioning and alignment equipment. The block can then be secured to the bone using fasteners. For instance, the cut guide block can be slidably mounted to an alignment guide, which can be mounted at an angle relative to an extramedullary guide or intramedullary rod. For tibial resection, an extramedullary guide is located relative to the patient's anatomy to provide proper alignment relative to the tibia, and a cut guide block is positioned on the proximal side of the tibia. Similarly, an intramedullary rod can be inserted into a pre-drilled hole in the intramedullary canal of the tibia to provide anatomic alignment with a cut guide block positioned on the proximal side of the tibia. For preparation of resection of the femur, an intramedullary rod can be used that extends across the distal end of the femur and the cut guide block is positioned on the proximal the side of the femur. The cut guide block can be slid toward or away (medially-laterally) from the tibia or femur until it is properly positioned against the surface of the bone. The block can then be pinned to the bone using fasteners. The cut guide can be connected to the alignment guide using pin/hole connect mechanism.

U.S. Pat. No. 7,927,336 is directed toward a guide assembly for guiding cuts to a femur and tibia during a knee arthroplasty.

U.S. Patent Pub. No. 20070233138 is directed toward apparatuses and methods for arthroplastic surgery.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

When a cut guide is connected to the alignment guide using a pin/hole or dovetail mating connect mechanisms, such connections can be prone to problems with binding. These connections also requires expensive manufacturing control on pins and holes, or dovetail features for the cut guide and the alignment guide. This patent application describes a quick connect mechanism, such as can include a cone lock, which can provide certain advantages, as explained herein.

Figure 1:
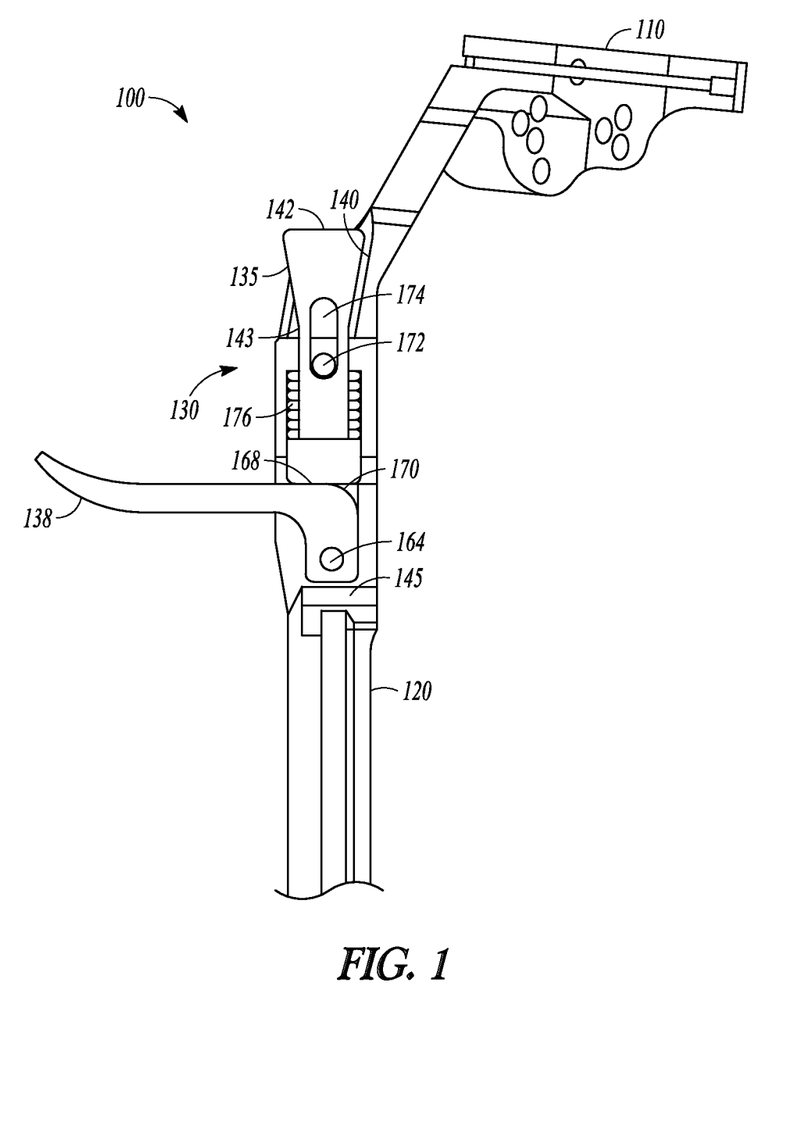
FIG. 1 shows a cross-section view of a connect mechanism, in a lock open position, in accordance with an embodiment.
Figure 2:
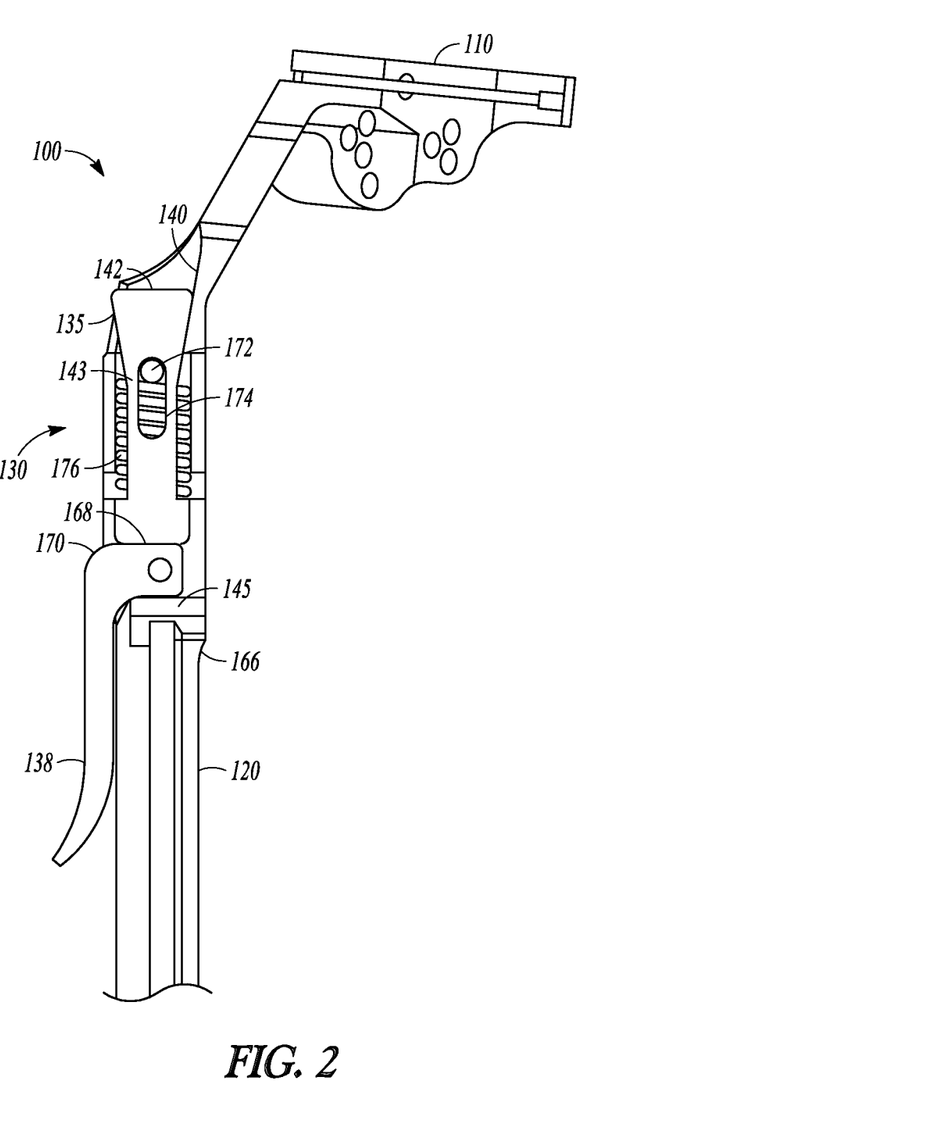
FIG. 2 shows an example of the apparatus of FIG. 1, in a lock closed position.

FIG. 1 shows an apparatus 100, in a lock open position, in accordance with an embodiment. FIG. 2 shows the apparatus 100, in a lock closed position. Apparatus 100 can include a cut guide 110 and an alignment guide 120. The apparatus 100 can include a connect mechanism 130 to connect the cut guide 110 to the alignment guide 120. The connect mechanism 130 can include a cone lock connect mechanism 130.

The cone lock connect mechanism 130 can include a slidable or other locking member 135 that can be slidably attached to the apparatus 100, such as to the alignment guide 120. A lever 138 can be mounted to the alignment guide 120 and can be functionally connected to the slidable locking member 135, such as to move the slidable locking member 135 up and down along the length of the alignment guide 120. The slidable locking member includes a cone-shaped upper portion 142. The cone-shaped upper portion 142 expands from a narrow diameter at a neck 143 to a wide upper diameter at the top of the cone-shaped upper portion 142.

The cut guide 110 can include a locking area 140 that can have an internal cone-shaped surface that can be configured to receive the cone-shaped upper portion 142 of the slidable locking member 135.

The slidable lock member 135 can include a groove 174 that rides along a pin 172. Slidable locking member 135 can be spring-biased by a spring 176 such that the slidable locking member 135 is biased downward toward the locked closed potion (FIG. 2).

A lever 138 rotates around a pin 164. When the lever 138 is put into the lock closed position (FIG. 2), the cone-shaped upper portion 142 slides down into and frictionally engages with the internal cone-shaped surface of locking area 140. The cone-shaped upper portion 142 and the locking area 140 have sloping surfaces that allow the mechanism to lock down medial/lateral, anterior/posterior, proximal/distal positions securely. Additionally, it locks down varus/valgus and anterior/posterior slopes. The shape does allow for internal/external rotation (transverse plane), which is a desired freedom. The cone shape as oriented in the present example locks down all of these positions and orientations as required. In some examples, the cone shape can range between 5 to 85 degrees. A smaller angle lends itself to a light holding force to mate the two cone features. As the angle increases, a larger holding force is required to lock the two geometries together securely.

The lever 138 can be shaped to lock open and lock closed, such as using a detent that can be formed by an abutment 145 of the alignment guide 120, which can inhibit or prevent rotation of the lever 138 until an applicable force is applied.

In operation, the release lever 138 can be rotated upwards about the pivot pin 164 (which can be fixed relative to a proximal tube 166 of the alignment guide 120), such as to slide the slidable locking member 135 upward by a cam surface 170 of the lever against a bottom surface 168 of the slidable locking member 135. The slidable locking member 135 slides upward such as to a point at which the slidable locking member 135 holds in an open position due to a flat end surface of the release lever 138 against abutment 145. Once held in the open position, the tibial cut guide 110 can be installed, such as transversely under the cone shape upper portion 142. In an example, the locking mechanism includes the male cone shape upper portion 142 that mates to a complementary female cone shape on the inner surface of the locking area 140 on the tibial cut guide 110. Once positioned roughly concentrically, the release lever 138 can be rotated downwards about the pivot pin 164, such as to apply a locking spring force to secure the tibial cut guide 110 to the top of the proximal tube 166. When in the locked closed position, the bottom 168 and the abutment 145 keep the lever in a lock closed position, and the upper portion 142 frictionally engages the locking area 140.

The slidable locking member 135 can be guided between the outer dimension (O.D.) of the slidable locking member 135 and the inner dimension (I.D.) of a hole in a proximal tube 166 of the alignment guide 120. The slidable locking member 135 can be guide assisted by a pin 172 that can be integral to the proximal tube 166. This pin 172 can help inhibit or prevent rotation of the slidable locking member 135 about the vertical axis. This pin 172 can act as a stop, such as for a spring 176 relative to the proximal tube 166. The other end of the spring 176 can be stopped relative to the bottom of the slidable locking member 135.

In an example, the cone angle at upper portion 142 can be anywhere from 0 degrees to 90 degrees. One example uses a range of between about 5 degrees to about 85 degrees. In an example, an embodiment can use a cone at a 10 degree cone angle.

The cut guide 110 can provide a lock down connection to the tibial alignment guide 120. This can permit a lock down of the cut guide 110 to the tibial alignment guide 120 in the sagittal and coronal planes using a reasonable amount of locking force. Additionally, it can allow for lock down in the transverse plane, but can allow for rotation on the same plane. For example, the apparatus can be configured to permit a transverse plane rotation of the cut block due to the cone shapes of the upper portion 142 and the complementary locking area 140.

One need for a cut guide to tibial alignment guide attachment can be for anterior removal of the tibial alignment guide from pinned block. In one past approach, modular connections of tibial cut guides can be made through either a dovetail or pin/hole engagement. However, these types of mechanisms can be problematic as they can easily loosen or bind up during alignment guide manipulation.

One feature that can be provided by the present system is a quick release for lock down. For ease of use in the operating room, it is helpful for the connection of the alignment guide 120 to the cut guide 110 be quick such that it need not require any additional tools or time consuming procedures. It can also be helpful that the release mechanism can be able to overcome the potential for binding.

An embodiment of apparatus 100 can include a lock open feature. To facilitate removal of the tibial alignment guide 120 from a pinned cut guide block, it can be helpful to be able to keep the release mechanism locked open (FIG. 1) such as to facilitate subsequent guide removal operations. Here, the end of lever 138 is abutted against abutment 145 and cam surface 170 rests against the bottom surface 168. This locks open the device until an overcoming force is applied to the lever 138. This facilitates removal of the tibial alignment guide 120 from a pinned cut guide block 110.

Using the embodiments discussed herein, the present connect mechanism can be easier to manufacture and it can be easier to control design tolerance over pin/hole type connections. The cone-lock mechanisms described herein can help eliminate design clearances that are required for pin/hole/hook style mechanism. Also, the present embodiments can allow for transverse plane rotation of the cut block. The present embodiments can help avoid binding. The mechanism can include a positive lock open feature such as to facilitate installation and removal.

Figure 3:
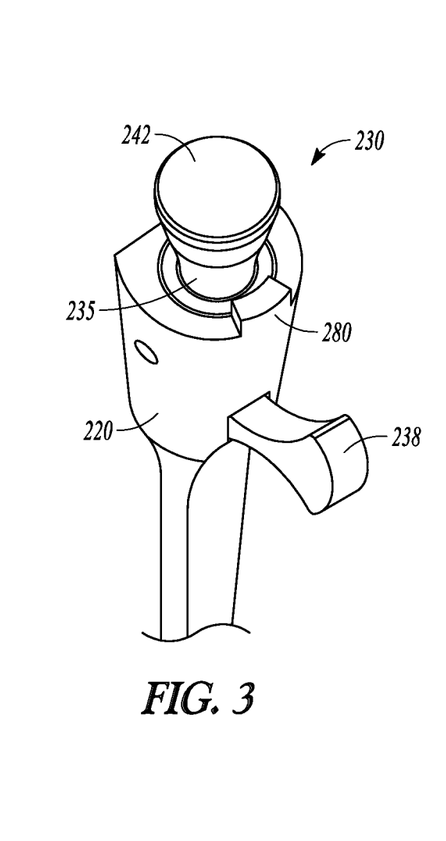
FIG. 3 shows an example of a top perspective view of a cone lock mechanism, in accordance with an embodiment.

FIG. 3 shows an example of a top perspective view of a cone lock mechanism 230 on an alignment guide 220, in accordance with an embodiment. The cone-lock mechanism 230 is shown in a lock open position. The cone lock mechanism 230 can include any of the features discussed herein for mechanism 130, and the above discussion is incorporated herein by reference.

Figure 4:
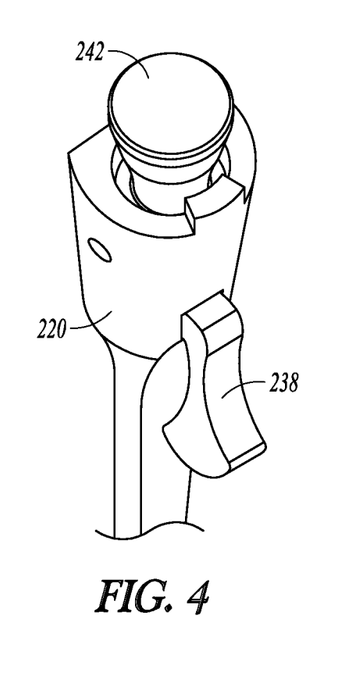
FIG. 4 shows an example of the cone lock mechanism of FIG. 3, in a lock closed position, in accordance with an embodiment

FIG. 4 shows an example of the cone lock mechanism 230, in a lock closed position. A lever 238 can be utilized, such as to translate a slidable member 235 up or down along the body of the alignment guide 220, such as to raise or lower an upper cone-shaped portion 242 of the lock mechanism 230. This example can include an abutment 280, which can engage with a cut guide, such as will be explained below.

Figure 5:
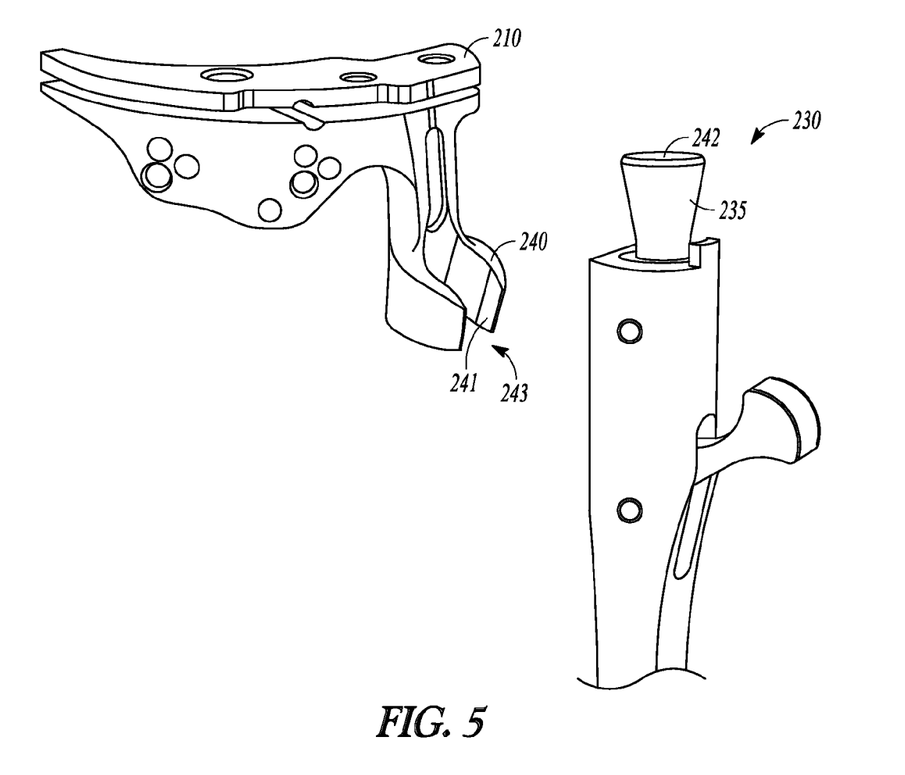
FIG. 5 shows an example of a cut guide and a cone lock mechanism, in accordance with an embodiment.
Figure 6:
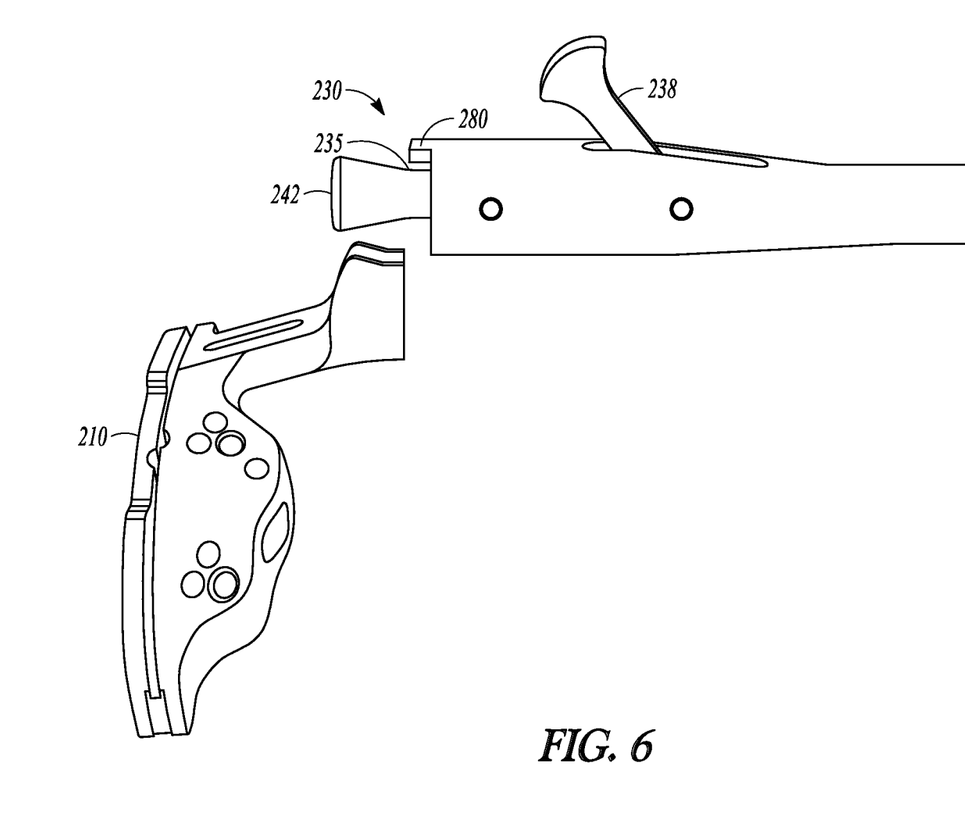
FIG. 6 shows an example of the cut guide being mounted to the cone lock mechanism of an alignment guide.
Figure 7:
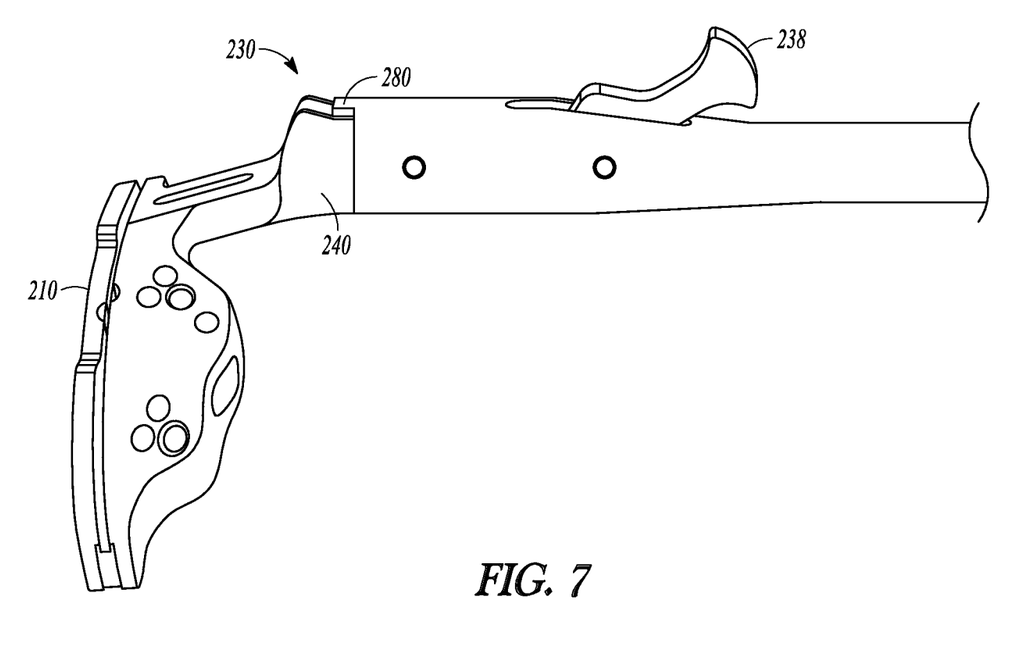
FIG. 7 shows an example of the cut guide mounted in a lock closed position to the cone lock mechanism of an alignment guide.

FIGS. 5-7 show further details of the present apparatus. FIG. 5 shows an example of a cut guide 210, in accordance with an embodiment; FIG. 6 shows an example of the cut guide 210 being mounted to the alignment guide 220, such as using the cone lock mechanism 230; and FIG. 7 shows an example of the cut guide 210 mounted in a lock closed position to the cone lock mechanism 230 of the alignment guide 220. The cut guide 210 can include a rear locking area 240 having a cone-shaped inner surface 241, such as to engage with the cone-shaped portion 242 of the cone lock mechanism 230. An anterior gap 243 can allow the locking area 240 to slip around the cone-shaped portion 242 of slidable member 235 at the neck area 243. The lever 238 rotates down to lock the cut guide 210 into place atop the alignment guide 220. The abutment 280 is located within the anterior gap 243.

Figure 8:
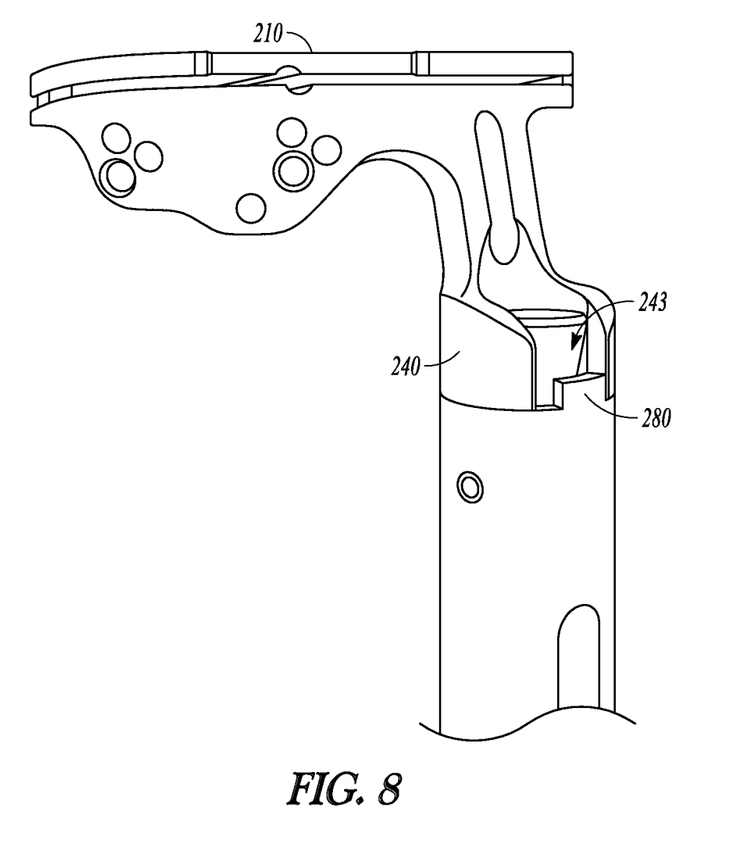
FIG. 8 shows an example of the cut guide mounted in a lock closed position to the cone lock mechanism of an alignment guide.

FIG. 8 shows an example of an anterior view of the apparatus. The anterior gap 243 can allow some transverse plane rotation of the cut guide 210 about the axis of the cone. Abutment 280 can be smaller than the gap 243 and can be dimensioned to help inhibit or prevent too much movement in either direction.

Figure 9:
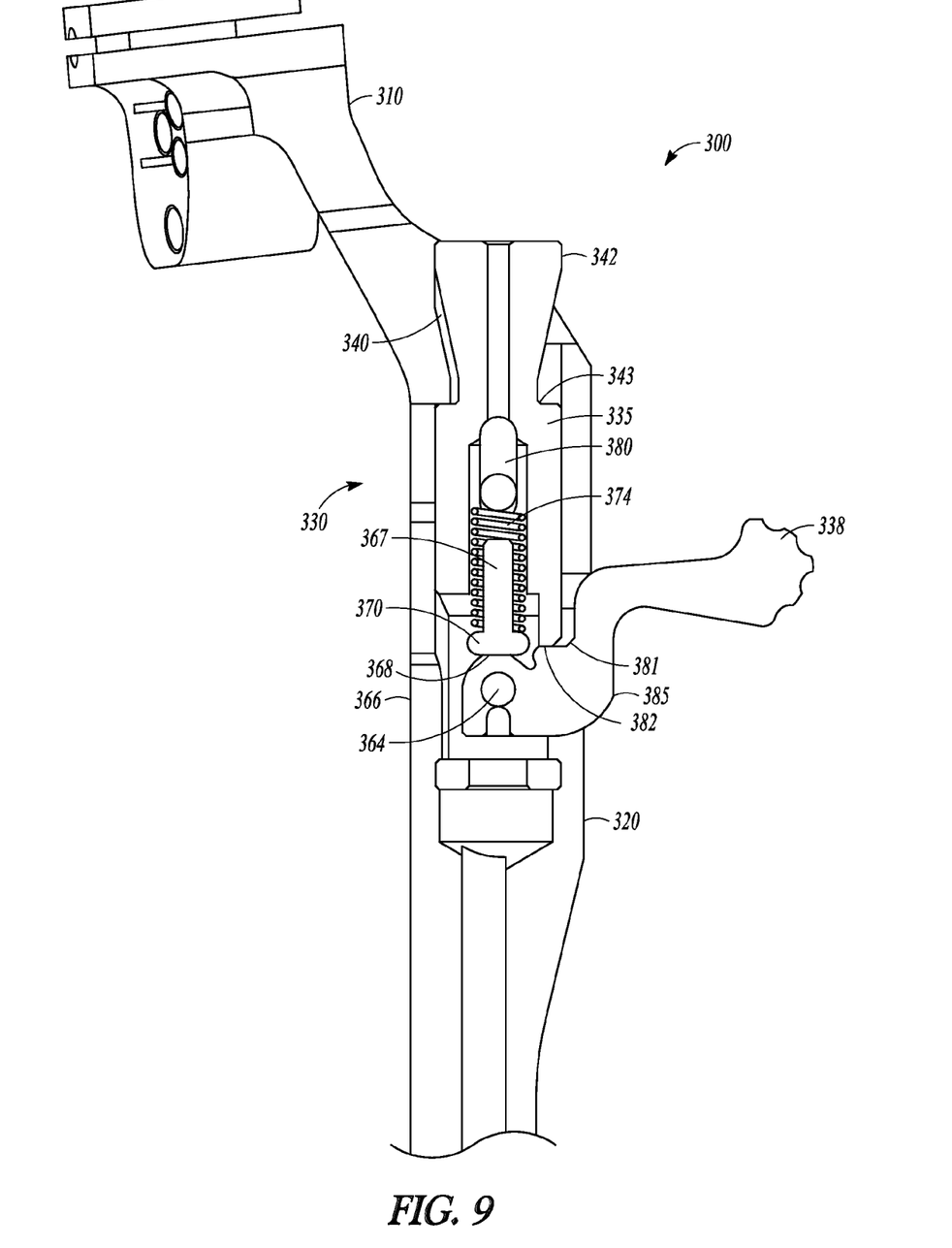
FIG. 9 shows a cross-section view of a connect mechanism, in a lock open position, in accordance with an embodiment.
Figure 10:
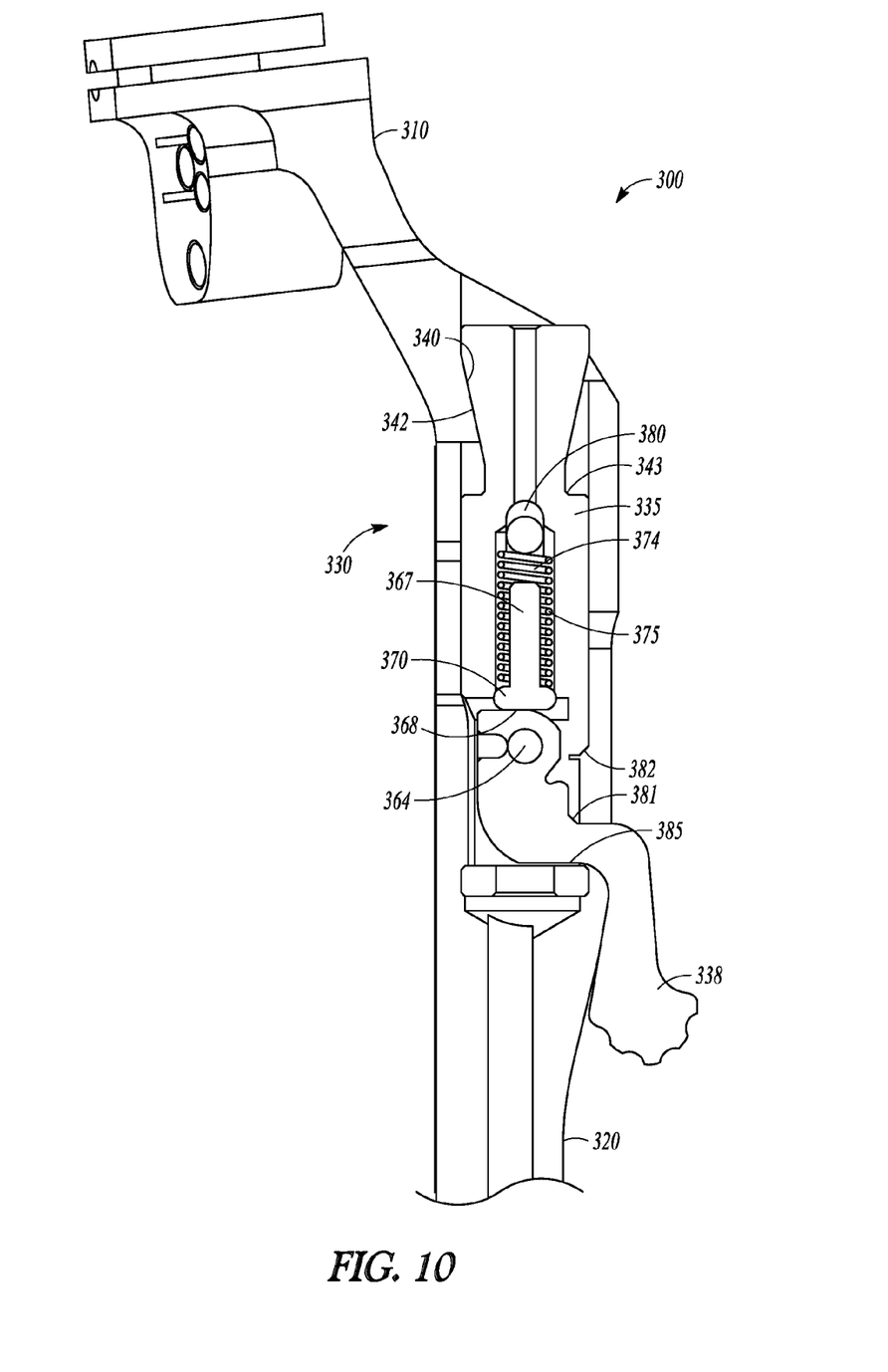
FIG. 10 shows an example of the apparatus of FIG. 9, in a lock closed position.

FIG. 9 shows an apparatus 300, in a lock open position, in accordance with an embodiment. FIG. 10 shows the apparatus 300, in a lock closed position. Apparatus 300 can include a cut guide 310 and an alignment guide 320. The apparatus 300 can include a connect mechanism 330 to connect the cut guide 310 to the alignment guide 320. The connect mechanism 330 can include a cone lock connect mechanism 330.

The cone lock connect mechanism 330 can include a slidable or other locking member 335 that can be slidably attached to the apparatus 300, such as to the alignment guide 320. A lever 338 can be mounted to the alignment guide 320 and can be functionally connected to the slidable locking member 335, such as to move the slidable locking member 335 up and down along the length of the alignment guide 320.

The cut guide 310 can include a locking area 340 that can have an internal cone-shaped surface that can be configured to receive a cone-shaped upper portion 342 of the slidable locking member 335. When the lever 338 is put into the lock closed position (FIG. 10), the cone-shaped upper portion 342 slides down into and frictionally engages with the internal cone-shaped surface of locking area 340. The cone-shaped upper portion 342 and the locking area 340 have sloping surfaces that allow the mechanism to lock down medial/lateral, anterior/posterior, proximal/distal positions securely. Additionally, it locks down varus/valgus and anterior/posterior slopes. The shape does allow for internal/external rotation (transverse plane), which is a desired freedom. The cone shape as oriented in the present example locks down all of these positions and orientations as required. In some examples, the cone shape can range between 5 to 85 degrees. A smaller angle lends itself to a light holding force to mate the two cone features. As the angle increases, a larger holding force is required to lock the two geometries together securely.

The lever 338 can be shaped to lock open and lock closed, such as using a detent that can be formed by abutments 345, 382 and a bottom surface 368 of the locking member 335 acting against cam surface 381, 385, and 370 of the lever 338. These structures can inhibit or prevent rotation of the lever 338 until an applicable force is applied. In the lock open position (FIG. 10), the detent is formed by the force of the surface 368 of a pin 367, which is biased by a spring 374, against a surface 370 of the lever 338.

In operation, the release lever 338 can be rotated upwards about a pivot pin 364 (which can be fixed relative to a proximal tube 366 of the alignment guide 320), such as to slide the slidable locking member 335 upwards due to the cam force of the lever surface 381 against the abutment 382 of the slidable locking member 335. Once held in the lock open position, the tibial cut guide 310 can be installed, such as transversely under the cone shape upper portion 342. In an example, the male cone shape upper portion 342 can include a complementary female cone shape on the inner surface of the locking area 340 on the tibial cut guide 310. Once positioned roughly concentrically, the release lever 338 can be rotated downwards about the pivot pin 364, such that a lower cam surface 385 of the lever pushes against abutment 345 to push the slidable lockable member 335 downward to secure the tibial cut guide 310 to the top of alignment guide 320.

The slidable locking member 335 can be guided between the outer dimension (O.D.) of the slidable locking member 335 and the inner dimension (I.D.) of a hole in a proximal tube 366 of the alignment guide 320.

In an example, the cone angle at upper portion 342 can be anywhere from 0 degrees to 90 degrees. One example uses a range of between about 5 degrees to about 85 degrees. In an example, an embodiment can use a cone at a 10 degree cone angle.

The cut guide 310 can provide a lock down connection to the tibial alignment guide 320. This can permit a lock down of the cut guide 310 to the tibial alignment guide 320 in the sagittal and coronal planes using a reasonable amount of locking force. Additionally, it can allow for lock down in the transverse plane, but can allow for rotation on the same plane. For example, the apparatus can be configured to permit a transverse plane rotation of the cut block.

Figure 11:
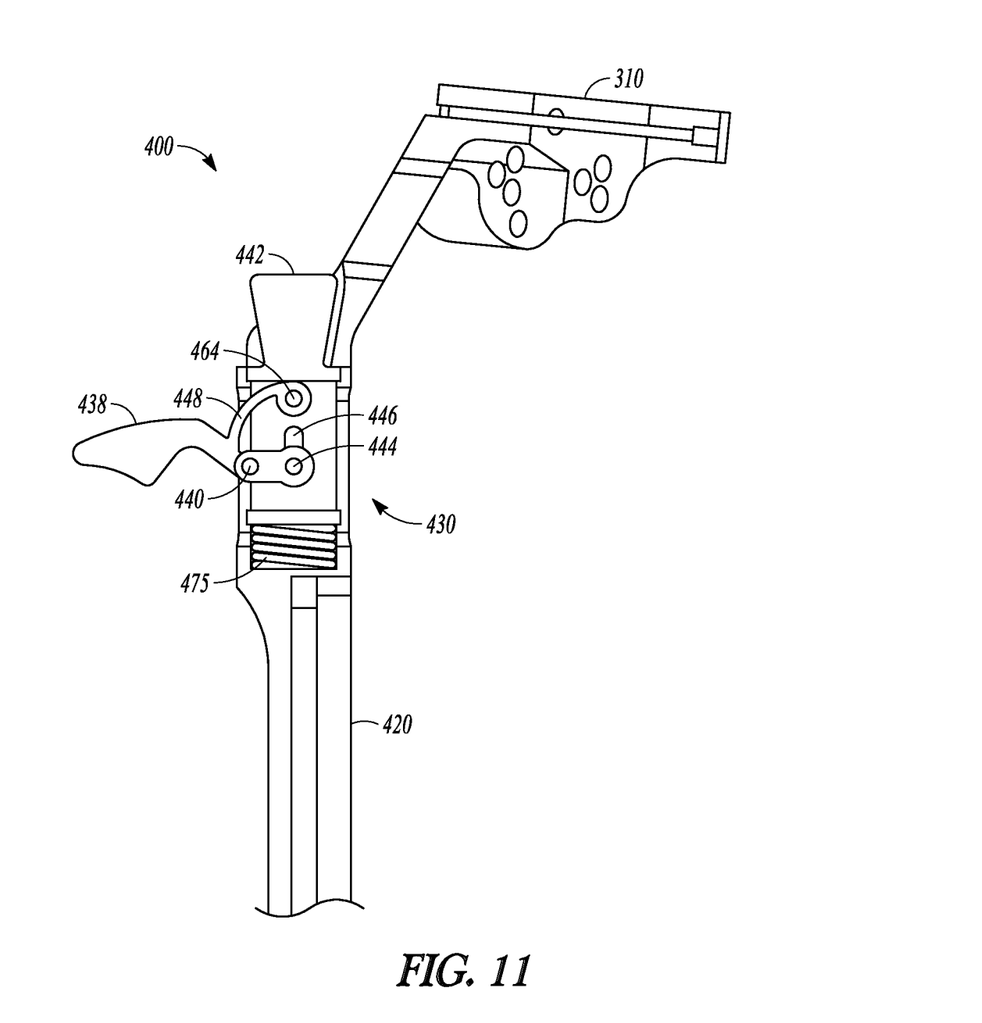
FIG. 11 shows a cross-section view of a connect mechanism, in a lock open position, in accordance with an embodiment.
Figure 12:
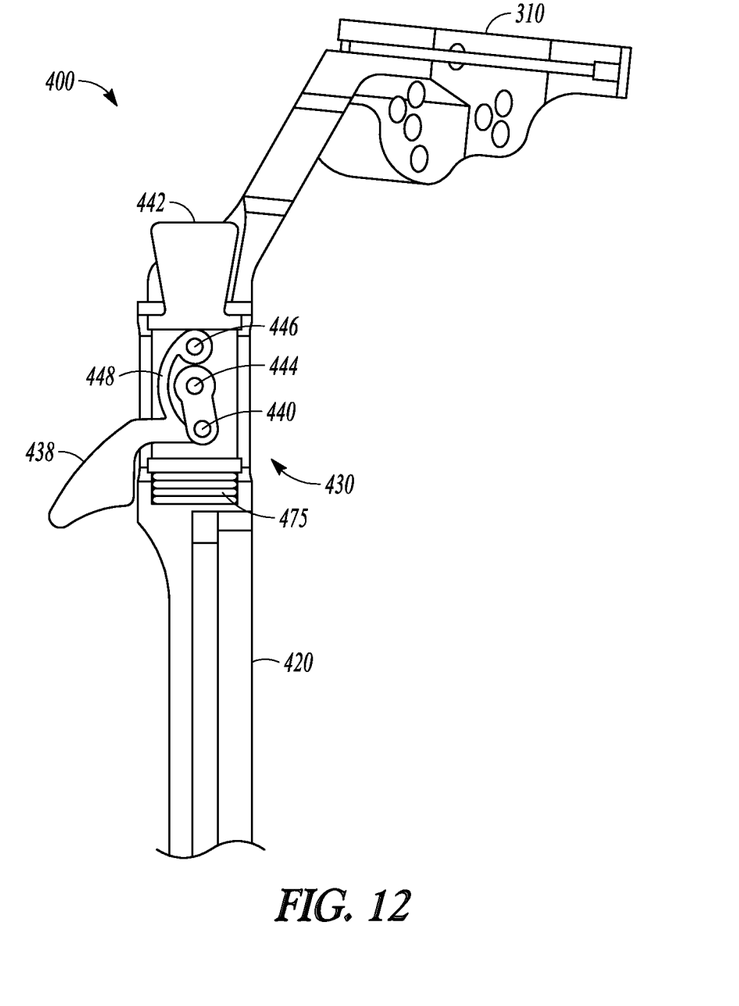
FIG. 12 shows an example of the apparatus of FIG. 11, in a lock closed position.

FIG. 11 shows an apparatus 400, in a lock open position, in accordance with an embodiment; and FIG. 12 shows the apparatus 400, in a lock closed position. Apparatus 400 can include a cut guide 310 and an alignment guide 420. The apparatus 400 can include a connect mechanism 430 to connect the cut guide 310 to the alignment guide 420. The connect mechanism 430 can include a cone lock connect mechanism 430. Certain details of apparatus 400 are similar to features discussed above for apparatuses 100, 200, and 300 and certain details will be omitted for sake of clarity. However, the above discussions are incorporated herein by reference.

The cone lock connect mechanism 430 can include a slidable or other locking member 435 that can be slidably attached to the alignment guide 420. A lever 438 can be mounted to the alignment guide 420 and can be functionally connected to the slidable locking member 435, such as to move the slidable locking member 435 up and down along the length of the alignment guide 420. The slidable locking member includes a cone-shaped upper portion 442. The cone-shaped upper portion 442 expands from a narrow diameter at a neck 443 to a wide upper diameter at the top of the cone-shaped upper portion 442.

The cut guide 310 can include a locking area that can have an internal cone-shaped surface that can be configured to receive the cone-shaped upper portion 442 of the slidable locking member 435.

Slidable locking member 435 can be spring-biased by a spring 475 such that the slidable locking member 435 is biased upward toward the locked open position (FIG. 11).

A lever 438 rotates around a pin 464 coupled to the slidable locking member 435. When the lever 438 is put into the lock closed position (FIG. 12), the cone-shaped upper portion 442 slides down into and frictionally engages with the internal cone-shaped surface of the locking area. The cone-shaped upper portion 442 and the locking area have sloping surfaces that allow the mechanism to lock down medial/lateral, anterior/posterior, proximal/distal positions securely. Additionally, it locks down varus/valgus and anterior/posterior slopes. The shape does allow for internal/external rotation (transverse plane), which is a desired freedom. The cone shape as oriented in the present example locks down all of these positions and orientations as required. In some examples, the cone shape can range between 5 to 85 degrees. A smaller angle lends itself to a light holding force to mate the two cone features. As the angle increases, a larger holding force is required to lock the two geometries together securely.

The lever 438 can be shaped to lock open and lock closed, such as using a detent that can be formed by an over-center cantilever structure between lever 438 and a rotating member 445. The rotating member 445 is rotatably connected by a pin 444 to the alignment guide 420 and by a pin 440 to the lever 338. As the lever 438 rotates downward, pin 464 and slidable member 435 slide downwards towards the locked closed position. At the same time, a groove 446 in the slidable member 435 rides down the pin 444 and the rotating member 445 rotates. When the lever 438 is fully closed (FIG. 12), bottom pin 440 is in an over-center arrangement relative to pins 444 and 464. This structure can inhibit or prevent rotation of the lever 438 until an applicable force is applied. In one option, a back section 448 of the lever 438 can be thinner than the main portion of the lever and act as a leaf spring, taking up any tolerance variations in the device.

In operation, the release lever 438 can be rotated upwards about the pivot pin 464. The slidable locking member 435 slides upward such as to a point at which the slidable locking member 435 holds in an open position due to the spring 475. Once held in the open position, the tibial cut guide 310 can be installed, such as transversely under the cone shape upper portion 442. In an example, the locking mechanism includes the male cone shape upper portion 442 that mates to a complementary female cone shape on the inner surface of the locking area on the tibial cut guide 310. Once positioned roughly concentrically, the release lever 438 can be rotated downwards about the pivot pin 464, such as to apply a locking force to secure the tibial cut guide 310 to the top of the alignment guide 420. When in the locked closed position, the over-center arrangement of lever 438 keeps the lever in a lock closed position, and the upper portion 442 frictionally engages the locking area of the cut guide 310.

The slidable locking member 435 can be guided between the outer dimension (O.D.) of the slidable locking member 435 and the inner dimension (I.D.) of a hole in a proximal tube of the alignment guide 420.

In an example, the cone angle at upper portion 442 can be anywhere from 0 degrees to 90 degrees. One example uses a range of between about 5 degrees to about 85 degrees. In an example, an embodiment can use a cone at a 10 degree cone angle.

The cut guide 310 can provide a lock down connection to the tibial alignment guide 420. This can permit a lock down of the cut guide 310 to the tibial alignment guide 420 in the sagittal and coronal planes using a reasonable amount of locking force. Additionally, it can allow for lock down in the transverse plane, but can allow for rotation on the same plane. For example, the apparatus can be configured to permit a transverse plane rotation of the cut block due to the cone shapes of the upper portion 442 and the complementary locking area of the cut guide 310.

Using the embodiments discussed herein, the present connect mechanism can be easier to manufacture and it can be easier to control design tolerance over pin/hole type connections. The cone-lock mechanisms described herein can help eliminate design clearances that are required for pin/hole/hook style mechanism. Also, the present embodiments can allow for transverse plane rotation of the cut block. The present embodiments can help avoid binding. The mechanism can include a positive lock open feature such as to facilitate installation and removal.

Figure 13:
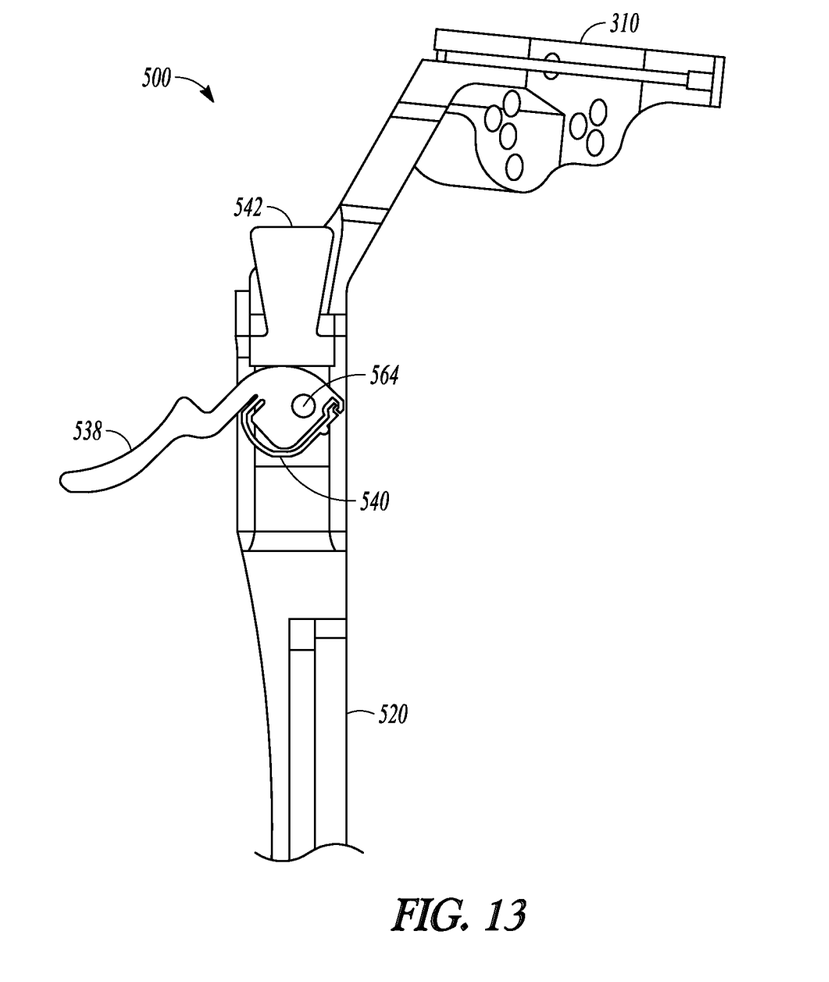
FIG. 13 shows a cross-section view of a connect mechanism, in a lock open position, in accordance with an embodiment.
Figure 14:
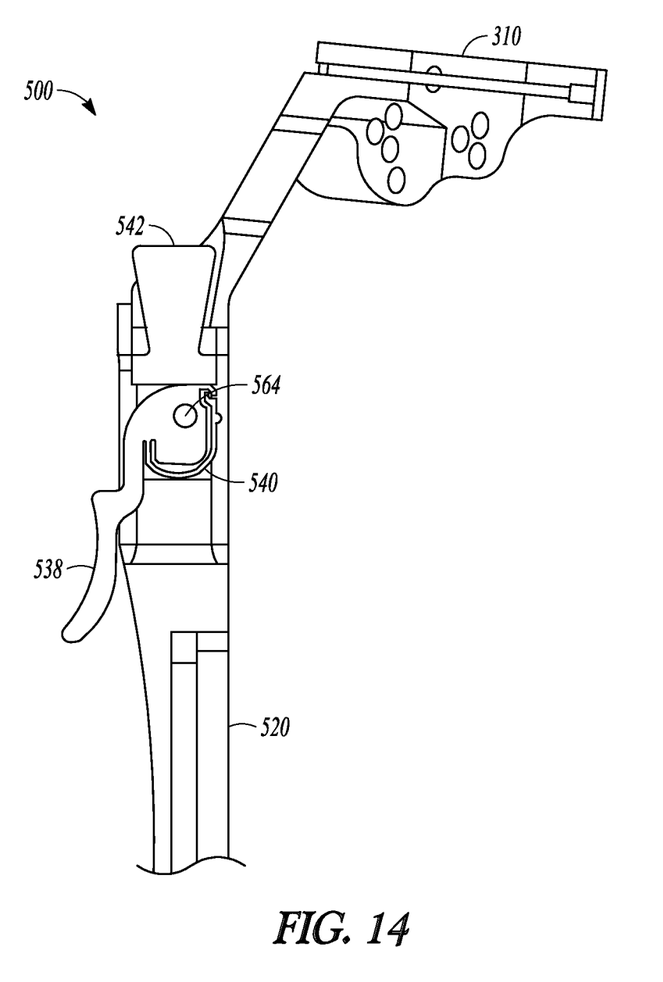
FIG. 14 shows an example of the apparatus of FIG. 13, in a lock closed position.

FIG. 13 shows an apparatus 500, in a lock open position, in accordance with an embodiment; and FIG. 14 shows the apparatus 500, in a lock closed position. Apparatus 500 can include a cut guide 310 and an alignment guide 520. The apparatus 500 can include a connect mechanism to connect the cut guide 310 to the alignment guide 520. The connect mechanism can include a cone lock connect mechanism. Certain details of apparatus 500 are similar to features discussed above for apparatuses 100, 200, 300, and 400 and certain details will be omitted for sake of clarity. However, the above discussions are incorporated herein by reference.

The cone lock connect mechanism can include a slidable or other locking member that can be slidably attached to the alignment guide 520. A lever 538 can be mounted to the alignment guide 520 and can be functionally connected to the slidable locking member, such as to move the slidable locking member up and down along the length of the alignment guide 520. The slidable locking member includes a cone-shaped upper portion 542. The cone-shaped upper portion 542 expands from a narrow diameter at a neck to a wide upper diameter at the top of the cone-shaped upper portion 542.

The cut guide 310 can include a locking area that can have an internal cone-shaped surface that can be configured to receive the cone-shaped upper portion 542 of the slidable locking member.

The lever 538 rotates around a pin 564 attached to the alignment guide 520. When the lever 538 is put into the lock closed position (FIG. 14), the cone-shaped upper portion 542 slides down into and frictionally engages with the internal cone-shaped surface of the locking area. The cone-shaped upper portion 542 and the locking area have sloping surfaces that allow the mechanism to lock down medial/lateral, anterior/posterior, proximal/distal positions securely. Additionally, it locks down varus/valgus and anterior/posterior slopes. The shape does allow for internal/external rotation (transverse plane), which is a desired freedom. The cone shape as oriented in the present example locks down all of these positions and orientations as required. In some examples, the cone shape can range between 5 to 85 degrees. A smaller angle lends itself to a light holding force to mate the two cone features. As the angle increases, a larger holding force is required to lock the two geometries together securely.

The lever 538 can be shaped to lock open and lock closed, such as using a detent that can be formed by a top cam surface of the lever acting against an abutment of the slidable member and a leaf spring 540 of the lever 538 acting against a bottom abutment surface of the slidable member. The leaf spring 540 can be formed by a cut-out region of the lever. As the lever 538 rotates downward, the bottom cam surface of the lever 538 contacts the abutment of the slidable member, driving the slidable member downwards towards the locked closed position. When the lever 538 is fully closed (FIG. 14), the top cam surface of the lever 538 abuts the abutment of the slidable member and the leaf spring 540 contacts the bottom abutment surface. This structure can inhibit or prevent rotation of the lever 538 until an applicable force is applied.

In operation, the release lever 538 can be rotated upwards about the pivot pin 564, which can be fixed relative to the alignment guide 520. The top cam surface of the lever 538 pushes upward on the abutment surface of the slidable member and the slidable locking member slides upward such as to a point at which the slidable locking member holds in an open position. Once held in the open position, the tibial cut guide 310 can be installed, such as transversely under the cone shape upper portion 542. In an example, the locking mechanism includes the male cone shape upper portion 542 that mates to a complementary female cone shape on the inner surface of the locking area on the tibial cut guide 310. Once positioned roughly concentrically, the release lever 538 can be rotated downwards about the pivot pin 564, such as to apply a locking force to secure the tibial cut guide 310 to the top of the alignment guide 520. When in the locked closed position, the top cam surface of the lever and the bottom leaf spring 530 of the lever contact the respective abutment surfaces and keep the lever 538 in a lock closed position, and the upper cone-shaped portion 542 frictionally engages the cone-shaped locking area of the cut guide 310.

The slidable locking member can be guided between the outer dimension (O.D.) of the slidable locking member and the inner dimension (I.D.) of a hole in a proximal tube of the alignment guide 520.

In an example, the cone angle at upper portion 542 can be anywhere from 0 degrees to 90 degrees. One example uses a range of between about 5 degrees to about 85 degrees. In an example, an embodiment can use a cone at a 10 degree cone angle.

The cut guide 310 can provide a lock down connection to the tibial alignment guide 520. This can permit a lock down of the cut guide 310 to the tibial alignment guide 520 in the sagittal and coronal planes using a reasonable amount of locking force. Additionally, it can allow for lock down in the transverse plane, but can allow for rotation on the same plane. For example, the apparatus can be configured to permit a transverse plane rotation of the cut block due to the cone shapes of the upper portion 542 and the complementary locking area of the cut guide 310.

Using the embodiments discussed herein, the present connect mechanism can be easier to manufacture and it can be easier to control design tolerance over pin/hole type connections. The cone-lock mechanisms described herein can help eliminate design clearances that are required for pin/hole/ hook style mechanism. Also, the present embodiments can allow for transverse plane rotation of the cut block. The present embodiments can help avoid binding. The mechanism can include a positive lock open feature such as to facilitate installation and removal.

In other examples of the present mechanisms described above, the cone can be oriented in any direction to allow for targeted degree of freedom locking For example, if the cone is oriented anteriorly/posteriorly, this configuration would lock down rotation in the transverse plane, but allow for rotation on the coronal plane, which might be desired in some future instrument embodiments.

Additional Notes

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body that divides the body into right and left halves.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. An apparatus for use in a surgical procedure on a patient, the apparatus including:
    a cut guide for guiding a surgical blade during the surgical procedure, the cut guide including a locking area;
    an alignment guide for aligning the cut guide in a desired position relative to the patient during the surgical procedure; and
    a connect mechanism coupled to the alignment guide and configured to selectively connect the cut guide to the alignment guide,
    wherein the connect mechanism includes a cone lock connect mechanism configured to engage with the cut guide locking area, the cone lock connect mechanism being a cone-shaped portion of the connect mechanism,
    wherein the connect mechanism further includes a slidable locking member coupled to the cone lock connect mechanism, the slidable locking member being slidable relative to the alignment guide between a first locked position in which the connect mechanism is configured to be fixedly coupled to the cut guide and a second unlocked position in which the cut guide can be removed from the connect mechanism, and
    wherein the connect mechanism includes a rotatable lever to control the slidable locking member between the first locked position and the second unlocked position upon rotation of the lever about a pivot pin coupled to the alignment guide.

2. The apparatus of claim 1, wherein the lever is configured to have a positive lock open position.

3. The apparatus of claim 1, wherein the locking portion of the cut guide includes an internal cone-shaped surface.

4. The apparatus of claim 1, wherein the apparatus is configured to permit a transverse plane rotation of the cut guide.

5. The apparatus of claim 1, wherein the locking area of the cut guide includes a gap and the connect mechanism includes an abutment, wherein when the cut guide is locked to the alignment guide, abutment is located within the gap.

6. An apparatus for use in a surgical procedure on a patient, the apparatus comprising:
    an alignment guide for aligning a cut guide in a desired position relative to the patient during the surgical procedure, the alignment guide coupled to an upper end of a connect mechanism configured to selectively connect the alignment guide to a cut guide, the cut guide configured to guide a surgical blade during the surgical procedure;

wherein the connect mechanism includes a connection member slidable relative to the alignment guide from an upper, open position to a lower, closed position, wherein the connection member includes a cone-shaped upper portion dimensioned to lock onto a corresponding internal cone-shaped surface of the cut guide, wherein in the upper, open position, the cut guide is free to be coupled or released from the alignment guide, and wherein in the lower, closed position, the connect mechanism is configured to fixedly lock the cut guide to the alignment guide, and wherein the connect mechanism includes a rotatable lever to control the slidable connection member up and down between the upper, open position and the lower, closed position by moving the connect mechanism along a length of the alignment guide upon rotation of the lever about a pivot pin coupled to the alignment guide.

7. The apparatus of claim 6, wherein the lever is configured to have a positive lock open position.

8. The apparatus of claim 6, wherein the connect mechanism is configured to permit a transverse plane rotation of the cut guide.

9. An apparatus for use in a surgical procedure on a patient, the apparatus including:

a cut guide for guiding a surgical blade during the surgical procedure, the cut guide including a locking area having an internal cone-shaped surface;

an alignment guide for aligning the cut guide in a desired position relative to the patient during the surgical procedure; and a connect mechanism coupled to the alignment guide and configured to selectively connect the cut guide to the alignment guide, wherein the connect mechanism includes a connection member slidable relative to the alignment guide from an upper, open position to a lower, closed position, wherein in the upper, open position, the cut guide is free to be coupled or released from the alignment guide, and wherein in the lower, closed position, the connect mechanism is configured to fixedly lock the cut guide to the alignment guide, wherein the connection member includes a cone-shaped upper portion dimensioned to lock onto the internal cone-shaped surface of the cut guide, and wherein the connect mechanism includes a rotatable lever to control the slidable connection member up and down along the length of the alignment guide between the upper, open position and the lower, closed position upon rotation of the lever about a pivot pin coupled to the alignment guide.

10. The apparatus of claim 9, wherein the lever is configured to have a positive lock open position.

11. The apparatus of claim 9, wherein the apparatus is configured to permit a transverse plane rotation of the cut guide.

12. The apparatus of claim 9, wherein the locking area of the cut guide includes a gap and the connect mechanism includes an abutment, wherein when the cut guide is locked to the alignment guide, abutment is located within the gap.

* * * * *